United States Patent [19]
Hudson et al.

[11] 3,940,732
[45] Feb. 24, 1976

[54] BUOYANT ELECTRODE AND SYSTEM FOR HIGH SPEED TOWING

[75] Inventors: John A. Hudson; Mitchell J. Yelverton, both of Panama City, Fla.

[73] Assignee: The United States of America as represented by the Secretary of the Navy, Washington, D.C.

[22] Filed: Mar. 30, 1970

[21] Appl. No.: 24,016

[52] U.S. Cl. .......... 340/4 E; 174/101.5; 114/235 B; 340/3 T
[51] Int. Cl.² ........................................ H01B 7/12
[58] Field of Search ............... 340/4, 4 E, 3 T, 7; 174/99 E, 99 R, 101.5; 114/235 A, 235 B

[56] References Cited
UNITED STATES PATENTS

| | | | |
|---|---|---|---|
| 2,549,777 | 4/1951 | Craig | 174/101.5 |
| 3,016,868 | 1/1962 | Haas | 114/235 |
| 3,155,768 | 11/1964 | Garshick | 174/101.5 |

*Primary Examiner*—Richard A. Farley
*Attorney, Agent, or Firm*—Richard S. Sciascia; Don D. Doty; William T. Skeer

[57] ABSTRACT

An electrode structure is disclosed which is particularly adapted for high density electrical current transfer to sea water. The electrode of the invention is adapted to be towed within sea water by an aircraft at high rates of speed. The electrode comprises a nonmetallic, high tensil strength central strain member, a concentric buoyant encasing layer, and an outer current carrying layer. Specific end construction is disclosed to compensate for differential electrolytic erosion of the electrode. Improved connector construction is described which provides for transmission of towing force to the electrode, as well as the transfer of electrical energy thereto. Further, specific terminating construction, which provides for the towing of both powered as well as nonpowered loads, is described.

8 Claims, 10 Drawing Figures

Distance Along Electrode
From Foreward End
(in Meters)

JOHN. A. HUDSON
MITCHELL J. YELVERTON
INVENTORS

BY William T. Skeer
Agent
Don D. Doty
Attorney

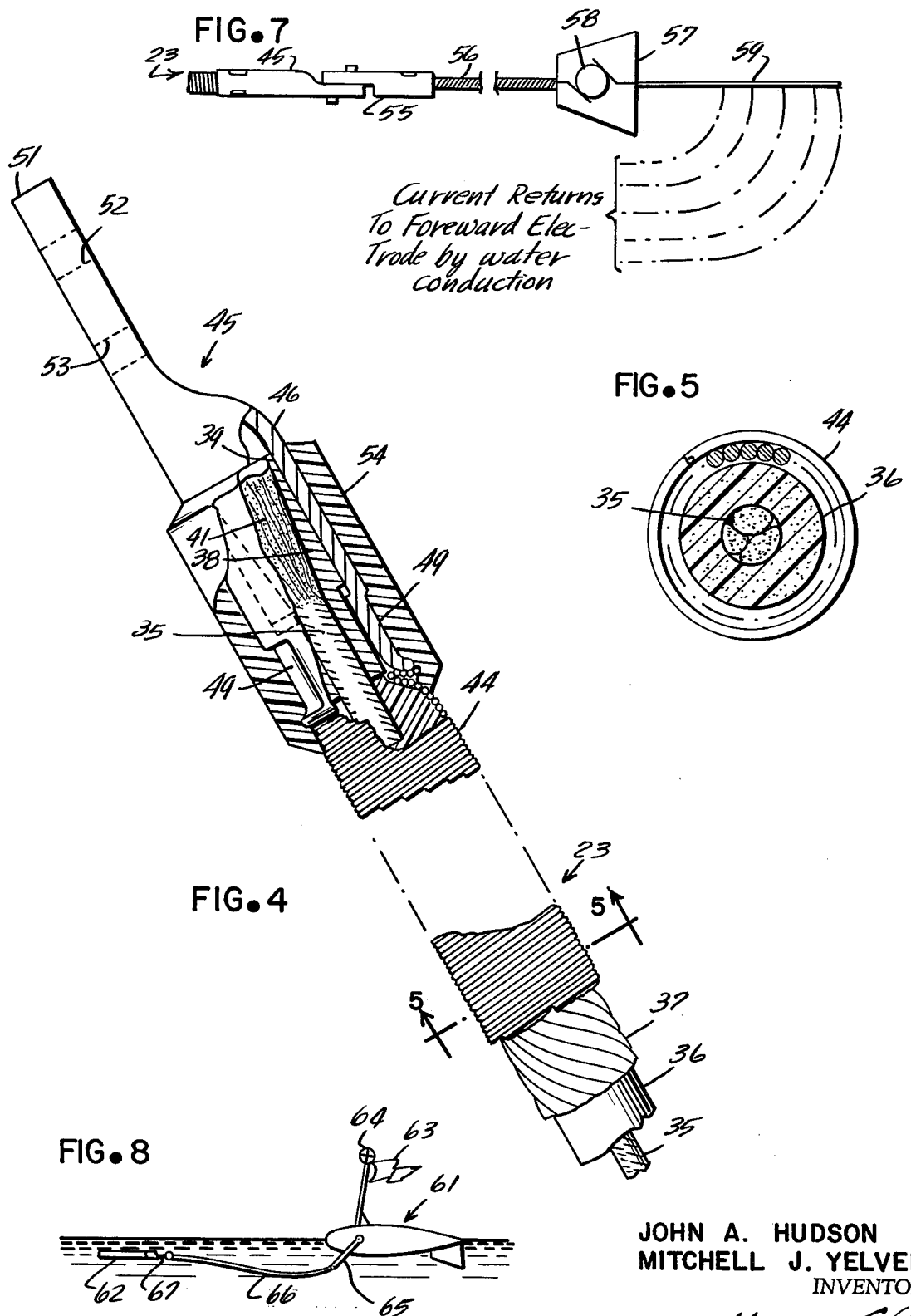

JOHN A. HUDSON
MITCHELL J. YELVERTON
INVENTOR.

BUOYANT ELECTRODE AND SYSTEM FOR HIGH SPEED TOWING

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention pertains to the Marine Sciences, and, more specifically, to the field of electro-oceanography. More explicitly, the invention pertains to the transfer of electrical power from a rapidly moving surface source into the sea. By way of further description of the field encompassed thereby, the invention pertains to an electrode structure useful for the transfer of electrical power into the sea water for producing magnetic disturbances therein. The electrode structure is particularly adapted for direct current applications.

In modern times, the oceanographic and naval sciences have placed increased reliance on aircraft as research vehicles. Specifially, the oceanographic mapping and minesweeping arts have increasingly made use of the high-powered, heavy-lift, rotary wing type of aircraft as a tow vehicle for their respective apparatus. The use of the aircraft to perform the vehicular duties has permitted a much larger area to be covered for a given expenditure of time, manpower, and money. However, the high cost-per-unit of time of aircraft operation has placed greater demands on the reliability of the equipment deployed by the aircraft.

Although weakening and breakage of the prior art electrodes have seldom occurred as a result of their being towed by slow-moving ships, boats, and the like, breakages thereof have been frequent and troublesome when towed by fast-moving aircraft. Hence, as a result of such fast towing, the electrodes of the prior art have had to be repaired quite often, something which is especially difficult and dangerous to do during military maneuvers. Moreover, such problems seem to be compounded when using the more modern direct current type of field generating electrodes of the prior art.

The development of suitable electrode structures for the aircraft towed oceanographic instrumentation has lagged behind the other components of the system. In the majority of instances, reliance is placed on electrode structure designed and configured to be streamed from much slower surface vessels. These units have proven to be unsatisfactory in many instances. The electrodes designed for surface towing have excessive bulk and weight for optimum deployment in aerial towed applications. Furthermore, and perhaps most importantly, the drag load imposed by these large and cumbersome devices have prevented their acceptance for use in aerial towed application.

Aerially towed electrodes of the prior art were simply lengths of uninsulated metallic copper cable. In addition to their heavy weight, such electrodes have a drag load nearly as great as their surface towed counterparts. Furthermore, the life expectancy of these prior art electrodes was short and unpredictable. The short life is due to a high rate of electrolytical erosion weakening the individual wire strands.

Prior art constructions have avoided the use of light-weight metals, since it is commonly supposed that the oxide products which are formed in static applications would coat the electrode, thereby electrically insulating it from the water and destroying its effectiveness.

Attempts to overcome these prior art deficiencies have resulted in buoyant coverings being placed over the copper cable electrodes. These prior art coverings were designed to permit the water to come into contact with the cable electrode and were satisfactory for alternating current applications. However, these coverings impaired the electrical efficiency especially for direct current applications by trapping ions and thereby creating a polarization voltage opposing the electrode voltage. Further, the thermal insulating properties of the covering cause the electrode to become heated by the current flow therein, further impairing its electrical performance. Also, the coverings prevented ready inspection of the electrode by maintenance personnel between operational deployments.

The aforementioned problems have posed continual application problems in the aerially conducted electro-oceanographic operations. This invention incorporates an electrode and electrode system which overcome these prior art difficulties.

SUMMARY OF THE INVENTION

The electrode of the invention is of a light weight construction with an especially configured exterior light metal exterior. Improved terminal construction is of effective design and is placed at both ends of said electrode to facilitate towing attachment thereto, as well as to permit the towing of auxiliary equipment thereby. A special serving of light metal wire at the ends thereof are especially effective in extending the useful life, as well as the predictability of the life, of the electrode of the invention. The electrode structure of the invention, although having a life expectancy of five times the prior art electrodes, is of such a low cost that it may be considered as expendable.

It is, accordingly, an object of this invention to provide an improved electro-oceanographic electrode.

A further object of this invention is to provide an electrode structure which may be towed at high speed in an ocean environment.

A further object of this invention is the provision of an expendable electrode which may be towed on the surface of a body of water by an aircraft tow vehicle.

A further object of this invention is the provision of a towed electrode assembly for electro-oceanographic applications with capability of towing an additional load therefrom.

A further object of this invention is the provision of a high speed towed electrode structure which is strong, lightweight and expendable.

Another object of this invention is the provision of an electrode structure which may be towed at high speeds to effectively sweep magnetic type marine mines.

Another object of the invention is to provide a magnetic sweep system having auxiliary devices to be used therewith, wherein the power consumed by the auxiliary device creates no interference with the electric magnetic sweep.

Another object of the invention is the provision of an electrode system to be towed by an aircraft to produce simultaneous magnetic and acoustic sweeps for marine mines.

A further object of this invention is the provision of an electrode structure to be towed at a high speed on the surface of the sea to sweep magnetically actuated mines located therein.

A further object of the invention is the provision of a magnetic sweep system having an auxiliary oceanographic device the electric current for which adds to the magnetic sweep current.

Other objects and many of the attendant advantages will be readily appreciated as the subject invention becomes better understood by reference to the following detailed description, when considered in conjunction with the accompanying drawings.

BRIEF DESCRIPTION OF THE DRAWINGS

FIG. 4 is a partial cutaway view of one end of the electrode of the invention;

FIG. 5 is a sectional view of the electrode of the invention taken along line 5—5 of FIG. 4;

FIG. 7 is an elevation view showing how the electrode may be used to provide towing propulsion and power supply to an auxiliary oceanographic device;

FIG. 8 is an elevation view showing how the electrode of the invention may be used to tow an unpowered oceanographic device;

DESCRIPTION OF THE PREFERRED EMBODIMENT

Figure 1:
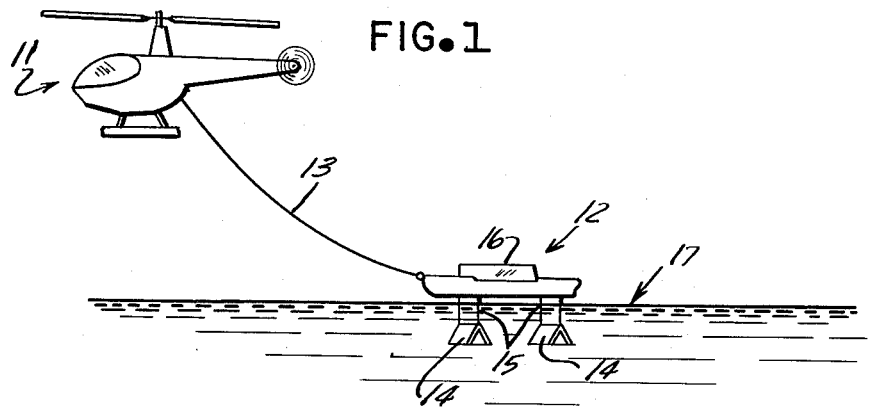
FIG. 1 is an illustration of a tow system employing the electrode of the invention.

Referring to FIG. 1, an aircraft 11 is shown towing a surface craft 12 via a tow cable 13. Surface craft 12 is supported in the water by means of hydrofoils 14 located on the lower portions of struts 15. Struts 15 are, of course, attached to surface craft 12, which supports a turbine driven electrical generator 16. Electrode structure, indicated generally at 17, streams aft of surface craft 12 to provide an electrical circuit for the electrical power produced by generator 16.

Aircraft 11 is shown as a rotary wing type of vehicle, but it should be understood that other draft vehicles might be used, if desired. Such vehicles might include ships, submarine vehicles, fixed wing aircraft, or surface effect vehicles, such as hovercraft and captive air vehicles. Similarly, other type of surface vehicle 12 than that shown might be used to support the electrical generating equipment. It is, of course, possible to place the electrical power generating equipment and the electrical instrumentation equipment within the draft vehicle and reduce the size of the surface craft 12 to that of a float. Power transmission difficulties makes such an arrangement impractical and favors the illustrated arrangement, shown in FIG. 1.

Figure 2:
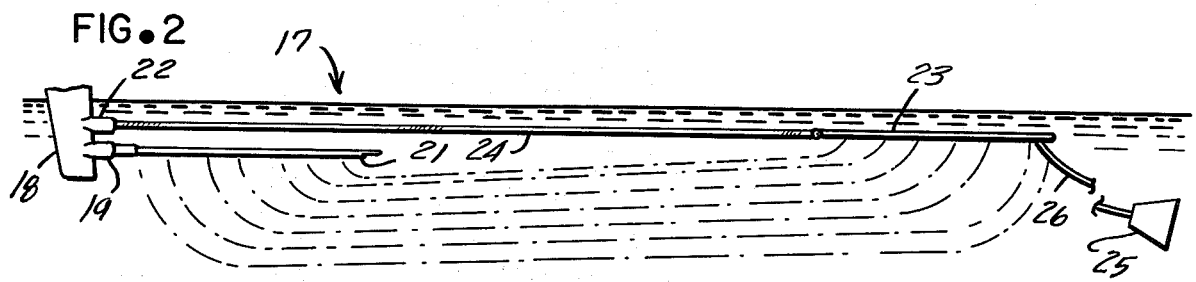
FIG. 2 is an illustration showing the electrode tow structure per se, with the current paths in the water shown for purposes of illustration.

Referring to FIG. 2, there is shown in greater detail the electrode structure 17, as it is deployed in a typical application. In this application, shown for purposes of illustration, the electrodes are used for minesweeping purposes, but this usage should be regarded as illustrative only, and not as a critical operational limitation. For example, the electrodes of the invention could be used in geophysical explorations, piscatological applications, and as a tactical weapon against personnel who are swimming, wading, or otherwise located in the water.

As shown, a power strut 18, which is attached to surface craft 12 so as to extend downwardly therefrom, has at its lower end a waterproof power connection 19. A foreward electrode 21 is attached to power connector 19 and extends aft therefrom to trail in the water as surface craft is towed along the surface by aircraft 11. Similarly, another power connector 22, located on the aft edge of power strut 18 above connector 19, provides towing and electrical connection for an aft electrode 23. Buoyant insulated conductor 24 connects aft electrode 23 to connector 22 for both towing and electrical power transfer thereto.

An auxiliary device, such as acoustic generator 25, may be streamed from aft electrode 23 by suitable flexible connection means 26, if desired, in a manner to be more fully explained herein.

The overall dimensions of electrodes 21 and 23 and their towing attachments may be altered to conform to the particular requirements. For minesweeping applications, an electrode length of 50 meters, and a spacing between the electrodes of 100 meters has proven satisfactory.

In operation, a massive electric current is caused to flow through buoyant conductor 24 to the aft electrode 23. The electric current is returned, via water conduction, to foreward electrode 21, as indicated by the broken lines in FIG. 2. In accordance with the well understood laws of electric power transfer, a magnetic field accompanies the concentrated electric current flow in buoyant conductor 24 which is uncancelled by the diffuse current flow in the sea water. The magnetic field, in turn extends outwardly to produce the desired magnetic interaction with the environment, in the illustrated instance, it is used to detonate marine mines that are sensitive to variations in magnetic fields.

Figure 3:
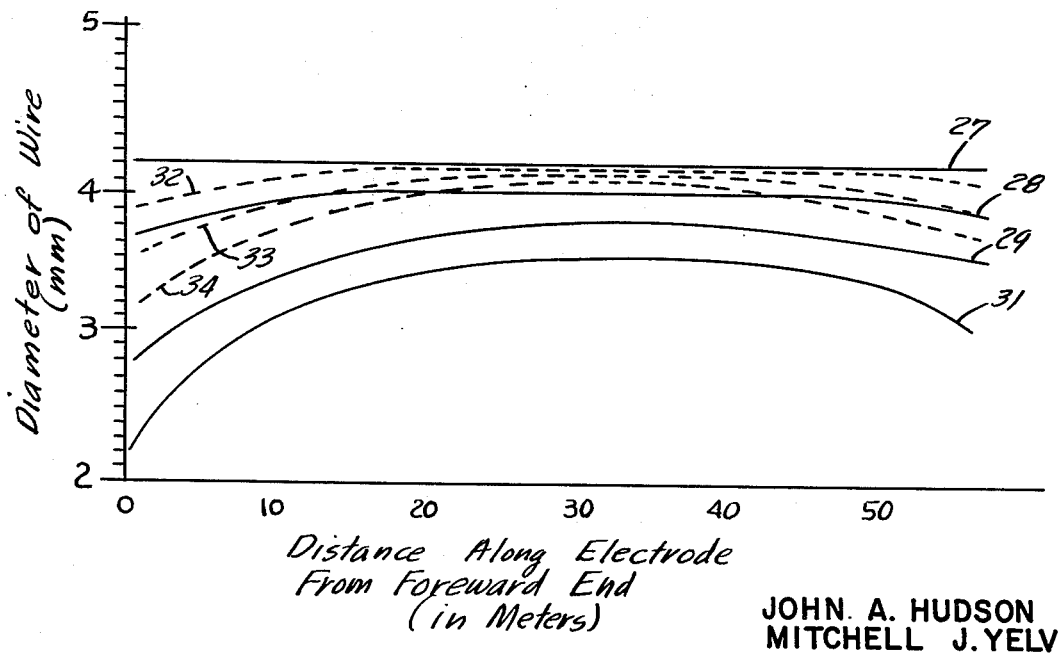
FIG. 3 is a graphic representation of certain performance characteristics of the electrode of the invention in comparison with prior art arrangements over a plurality of intervals of operation.

Referring to FIG. 3, the high rate of wear of prior art cable electrodes is graphically illustrated. Curves 27, 28, 29, and 31 represent the dimension of 4.2 mm strands of copper wire used in a cable electrode carrying 2,000 ampers of electrical current for periods of zero, 1, 2 and 4 hours, respectively. Under typical operational conditions this amounts to the loss of approximately 10 pounds of copper per hour on an electrode of 50 meters length and 75 mm diameter.

Curves 32, 33, and 34 represent the material losses experienced by a similarly dimensioned electrode of the invention for periods of 4, 8, and 16 hours respectively. The profound improvement over the prior art configuration is obvious.

The electrode of the invention is made of aluminum. Previously, aluminum was believed to be unsatisfactory for service as a sea water contacting electrode because of the formation of an insulating film of aluminum oxide ($Al_2O_3$). It was supposed that the oxide would soon insulate the electrode from the water, thereby increasing the resistance of the system and the power required for its operation. Such an insulating layer is formed in static conditions, but, apparently it is not formed at the high speeds at which the invention is practiced, since no increase in resistance has been observed, nor can the oxide film be detected after periods of use.

With reference to FIG. 3, it will be observed that the electroyltic erosion is greater at the ends and particularly at the foreward end of the electrode. This differential erosion, if uncorrected, weakens the electrode in an area where the maximum strength is required thereby promoting premature failure.

Referring to FIGS. 4 and 5, the electrode of the invention is shown in a partial cutaway end section. For purposes of explanation, the illustration may be considered to be electrode 23; however, it should be noted that, in most instances, electrodes 21 and 23 are identical. As shown, a central strain member 35 forms the core of electrode 23. Strain member 35 is, in the preferred embodiment, a suitable diameter rope made of a synthetic fibre such as nylon. A buoyant sleeve 36, made of cellular polyethylene, for example, surrounds strain member 35.

Buoyant sleeve 36, as the name suggests, provides the buoyant force which keeps the electrode assembly of the invention on or near the surface of the water in which it is disposed and in a horizontal attitude. Buoyant sleeve 36 is molded, or otherwise formed in place on central strain member 35. This assembly forms a very light and strong support for electricity conducting layer 37 disposed about the outer surface of buoyant sleeve 36.

Conductor layer 37 is made of a plurality of aluminum strands which are helically wound at a small angle about buoyant sleeve 36. The electrical contact with the water and power transfer thereto is provided by conductor layer 37. The outermost placement of conductor layer 37 facilitates electrical power transfer to the water as well, as the cooling of the electrode by direct exposure to the water. Additionally, the outermost placement of layer 37 permits visual inspection of the strands for electrolytic corrosion damage.

Figure 6:
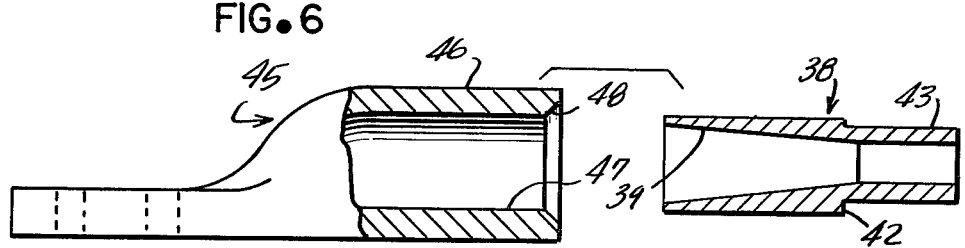
FIG. 6 is an exploded sectional view of the electrical connector used in the electrode structure of FIG. 4.

The terminal construction of electrode 23 is illustrated in FIGS. 4 and 6. The end of strain member 35 is placed through a central aperture in stop member 38 and spread apart in conical opening 39 in the one end thereof. Conical opening 39 is then filled with an epoxy type resin adhesive material which solidifies, to form a plug 41, and prevents withdrawal of strain member 35 from stop member 38. As shown at FIG. 6, a shoulder 42 on the opposite end of stop member 38 provides a reduced diameter portion 43 to receive conducting layer 37 thereon and to abut buoyant sleeve 36.

An aluminum wire serving 44 is formed of a single aluminum wire and is wrapped tightly about layer 37 thereby securing it to reduced diameter portion 38. Wire serving 44 extends a considerable length along electrode 23, for example about 16 meters. Stop member 38, with strain member 35, buoyant sleeve 36, conducting layer 37, and wire serving 44 attached thereto, is inserted in connector member 45.

Connector member 45 has a cylindrical portion 46 with an aperture 47 extending therein for receipt of stop member 38. A beveled edge 48 assists the insertion of the stop member 38, particularly with respect to serving 44 which sometimes requires some compressional force to be applied thereto to permit passage into aperture 47.

when stop member 38 is completely inserted within aperture 47, cylindrical portion 46 is mechanically deformed, i.e., crimped, to cause deformations 49 to be formed therein. As may be seen in FIG. 4, deformations 49 distort the inner wall of aperture 47 to cause it to close behind shoulder 42 to effectively prevent withdrawal of stop 38 and the electrode components secured thereto. This mechanical deformation causes electrical contact to be made between connector member 45 and conducting layer 34.

Connector 45 has, adjacent to cylindrical portion 46, a flattened portion 51. Two cylindrical apertures 52 and 53 pass through flattened portion 51. Apertures 52 and 53 receive threaded fasteners, not shown, to secure flattened portion 51 to a similarly shaped connector for mechanical and electrical union therewith. The end construction is completed with a molded synthetic rubber collar 54 which provides a waterproof seal and an anchoring point for an enclosing waterproof boot, not shown, to cover connector member 45 and its cooperating counterpart.

As previously noted in the discussion of electrolytic erosion, the rate of material loss is much greater at the ends of the electrode than in the central region. The aluminum wire serving 44 provides the source for the majority of the material removed from the electrode of the invention. The individual conductors comprising conducting layer 37 are thereby protected. Further, in the final stages of weakening the individual strands are strengthened against breakage and unfraying in the water by serving 44.

Both ends of electrode 23 may be terminated by the use of terminal means such as connector member 45. This permits the reversal of electrode 23 periodically to equalize the electrolytic erosion. Further, the use of a terminating connector member 45 permits the towing of an instrument or other device which uses electrical power in its operation in such a manner that instrument obtains its power from electrode 23. Such an arrangement is illustrated at FIG. 7.

Referring to FIG. 7, there is shown a towing and power supplying arrangement for streaming auxiliary oceanographic equipment from electrode 23. A connecting member 55 is secured to the aft connector 45 for towing thereby. An electrically insulated connecting cable 56 is attached to connector 55 and extends to the auxiliary oceanographic equipment towed thereby. For purposes of illustration, the device towed may be considered to be an acoustic generator 57 having an electric motor 58. Motor 58 may drive hammers, not shown, or other acoustic energy generating devices. Cable 56 is attached mechanically to the generator 57, and is electrically connected to motor 58 for electrical current supply thereto. The electrical return from the motor may be made through a water return path in a manner similar to the generation of the electromagnetic field by electrodes 21 and 23. For this purpose, an uninsulated return electrode 59 is streamed aft the acoustic generator 57. The current return to the foreward electrode is shown by the broken lines.

Although the towed device is described as an acoustic generator, it should be clear that other oceanographic devices may be similarly towed. Among the devices which may be so deployed are recording thermometers, salinity measuring devices and other survey and sampling apparatus. Similarly, motor 58 is only representative of operational electric loads which may be housed within the towed device. Others may include piezoelectric transducers, solid state circuit devices, and fluid testing apparatus, for example.

It will be appreciated by those skilled in the marine engineering and electro-oceanographic arts that the electric current used by the auxiliary device adds to the total field produced by the buoyant conductor 24. In prior art arrangements, when an auxiliary device was used in conjunction with a magnetic sweep, it was separately powered, and, in instances where the power consumption was appreciable, allowances had to be made for disturbances to the sweep field.

Alternatively, the electrode of the invention may be used to tow oceanographic instrument and operational loads which are electrically passive. Such an arrangement is illustrated at FIG. 8 where a marker float 61 is shown as being towed by an aft electrode 62. Such floats are useful in plotting course over which the electrodes were towed to thereby record the area swept by the towing of the electrodes. For this purpose, float 61 carries devices, such as pennet 63 and electromagnetic energy reflector 64, to enhance the visibility thereof. Marker float is attached to electrode 62 by a towing bridle 65, towing line 66 and shackle 67. Towing attachment may be made to the aft electrical connector member 45, or, alternatively a different type connector may be used which transmits only towing force. Such shackle and bridle attachment arrangements are familiar to those who are skilled in the marine engineering arts, and, being conventional arrangements, need not be discussed further herein.

Figure 9:
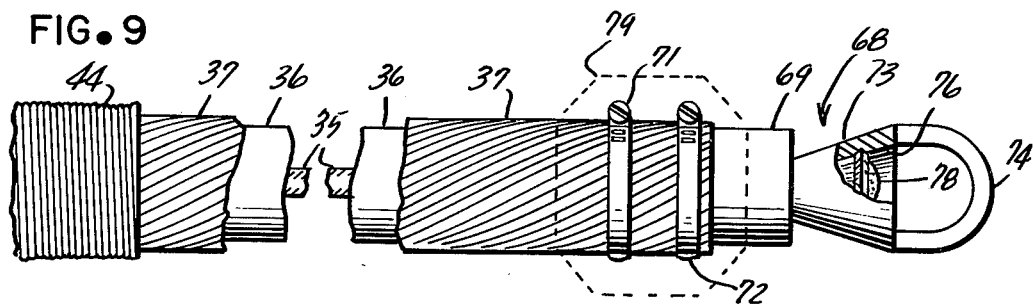
FIG. 9 is an elevation view of a modified electrode according to the invention for towing unpowered accessories.

Referring to FIG. 9, there is shown an electrode 62 made to tow passive loads in accordance with the invention. Like electrode 23, previously described, its foreward end terminates in an electrical connector member, not shown, and has an aluminum wire serving 44 bound about conducting layer 37. Likewise, a central strain member 35 and a buoyant sleeve 36 underlie conducting layer 37 in the same fashion as in the aforedescribed construction. However, at the aft end electrode 62 terminates in a towing eye 68. Since there is no electrical power transmitted by towing eye 68, conducting layer 37 is terminated slightly short of the end of electrode 62 leaving a buoyant sleeve segment 69 exposed thereat. Conducting layer 37 is bound to buoyant sleeve 35 by two compressional clamps 71 and 72. Central strain member 35 is secured to towing eye 68 in a fashion similar to the fashion that it was affixed to stop member 38.

Figure 10:
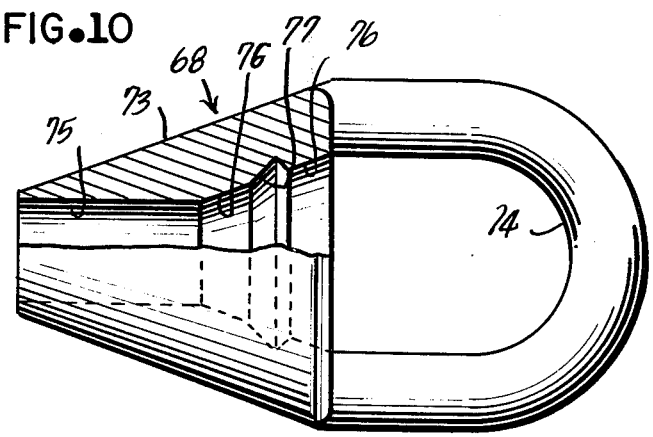
FIG. 10 is an elevation view, in partial section, showing the towing eye termination structure used in the electrode of FIG. 9.

Referring to FIG. 10, the construction of towing eye 68 and the manner of attaching central strain member 35 thereto will be more clearly understood. As shown, towing eye 68 comprises a conically tapered body portion 73 integrally joined with a closed U shaped eye loop 74. A cylindrical bore 75 on the conical axis communicates with a conically flared opening 76 to form a passageway through body member 73. A groove 77 extends circumferentially about the inner surface of conically shaped opening 76 to assist in the attachment of towing eye 68 to strain member 35.

In assemblying towing eye 68 to central strain member 35, the end of strain member 35 is passed through cylindrical bore 75 to communicate with conically flared opening 76. The individual strands of central strand member 35 are spread apart along the walls of conically flared openings 76. An epoxy type resin cement, or other suitable hardening cement, is placed in opening 76 to the depth necessary to cover groove 73. After hardening, this cement forms a plug 78, FIG. 9, which prevents separation of towing eye 68 from electrode 62.

As shown by broken lines in FIG. 9, clamps 71 and 72 may be enclosed in a molded rubber protecting collar 79 if desired. Collar 79 may be made of suitable synthetics, such as the synthetic rubber used in collar 49, and, like collar 49, may be used as a mounting surface for the securing of waterproof rubber sleeves and other protecting gear.

PREFERRED METHOD OF OPERATION

As suggested in the description of the preferred embodiment, the device of the invention is preferably utilized in connection with aircraft tow vehicles. The electrodes are assembled to the power strut 18, FIG. 2, with the auxiliary devices attached thereto. If the auxiliary device to be towed by the aft electrode requires electrical power, the type of electrode as designated by the reference numeral 23 is used. Should the auxiliary device require no electrical power for its operation, or should no auxiliary device be required, then either electrode 62 or 23 may be used as the aft electrode. Of course, either terminal construction may be used as an end construction on foreward electrode 21.

Surface craft 12, with the electrodes attached, is secured under aircraft 11. Aircraft 11 then transports the device to the selected operation site where the towing operation is to be conducted. When over the site, surface craft 12 is lowered to the water surface via tow cable 13. Foreward motion of the aircraft then propels the surface craft along the desired course.

In minesweeping operations, an auxiliary device, such as an acoustic generator, is frequently attached to the electrode structure to effect a simultaneous acoustic and electromagnetic sweep. It is understood that these devices may be streamed from the end of the aft electrode and electrically connected thereto, as discussed above, for derivation of operational potential therefrom. However, such auxiliary equipment is not limited to minesweeping, and it should be understood that other apparatus such as salinity, temperature, or other oceanographic measuring devices may be similarly streamed.

After a predetermined number of hours of use, the electrodes are routinely replaced. However, because of the exterior location of the conducting layer 37, inspection after each use is possible and excessive erosion or other damage which would warrant unscheduled electrode replacement may be detected.

The foregoing description taken together with the appended claims constitute a disclosure such as to enable a person skilled in the marine engineering arts and having the benefit of the teaching contained therein to make and use the invention. Further, the structure herein described meets the objects of invention, and generally constitutes a meritorious advance in the art unobvious to such a skilled worker not having the benefit of the teachings contained herein.

Obviously, other embodiments and modifications of the subject invention will readily come to the mind of one skilled in the art having the benefit of the teachings presented in the foregoing description and the drawings. It is, therefore, to be understood that this invention is not to be limited thereto and that said modifications and embodiments are intended to be included within the scope of the appended claims.

What is claimed is:

1. An improved oceanographic system adapted for being towed at high speed within a body of water for transferring electrical current thereto comprising:
    an electrode;
    central strain means disposed for effectively providing a central foundation for said electrode capable of withstanding high tensional loadings;
buoyant sleeve means surrounding said central strain means and substantially co-extensive therewith for providing a supporting force therefor;
a plurality of lightweight metal electrical conductor means placed in a predetermined pattern about the outer surface of said buoyant sleeve means, effectively forming a layer overlying said buoyant sleeve means for conduction of electricity therealong;
first connector means effectively connected to said central strain means at one end thereof for providing mechanical attachment thereto and effectively electrically connected to said plurality of electrical conductor means for electrical energy transfer therebetween;
lightweight conductor serving means effectively electrically and mechanically connected to said first connector means and disposed so as to be tightly wound about said predetermined pattern of the aforesaid plurality of lightweight metal electrical conductors and extending a predetermined distance therealong for providing retaining engagement thereof and electrical conduction therefrom;
second connector means effectively joined to the other end of said central strain means for attachment of auxiliary devices to be towed thereby;
insulated electrical conductor means effectively attached to said second connector means for current conducting cooperation therewith;
oceanographic instrument means effectively mechanically connected to said insulated electrical conductor means, so as to be towed thereby for performing predetermined oceanographic functions;
electrically operated means effectively attached to, and located within, said oceanographic instrument means and effectively electrically connected to said insulated electrical conductor means for activating said oceanographic means to perform said predetermined oceanographic functions; and
electrical current return electrode means effectively electrically connected to said electrically operated means, and effectively mechanically connected to said oceanographic instrument means, so as to be towed thereby, said electrical current return electrode means extending aft of said oceanographic instrument means and in electrical contact with said body of water for providing a current return path therethrough.

2. An improved oceanographic system according to claim 1 in which said central strain means comprises a non-metallic, synthetic fibre rope.

3. An improved oceanographic system according to claim 1 in which said buoyant sleeve means comprises a member made of cellular plastic material.

4. An improved oceanograhic system according to claim 1 in which said plurality of lightweight metal conductor means are made of aluminum.

5. An improved oceanographic system according to claim 1 in which said first connector means further comprises:
stop means having an aperture for passage of said central strain means therethrough and a conical opening communicating with said aperture, so as to receive the end of said central strain means and cement plug formed thereabout for attachment to said central strain means;
an aperture in said connector means for receiving said stop means; and
deformed walls engaging said stop means for preventing withdrawal thereof.

6. An oceanographic system according to claim 1 in which said lightweight conductor means is made of aluminum.

7. An improved oceanographic system according to claim 1 in which said second connector means comprises a towing eye which is effectively connected to said central strain member for towing an auxiliary load therefrom.

8. An improved oceanographic system adapted for being towed at high speed within a body of water for transferring electrical current thereto comprising:
first electrode means;
central strain means for providing a central foundation for said first electrode means capable of withstanding high tensional loadings;
buoyant sleeve means surrounding said central strain means and substantially co-extensive therewith for providing a supporting force therefor;
a plurality of lightweight metal electrical conductor means placed in a predetermined pattern about the outer surface of said buoyant sleeve means, effectively forming a layer overlying said buoyant sleeve means for conduction of electricity therealong;
first connector means effectively connected to said central strain means at one end thereof for providing mechanical attachment thereto and effectively electrically connected to said plurality of electrical conductor means for electrical energy transfer therebetween;
lightweight conductor serving means effectively electrically and mechanically connected to said first connector means and disposed so as to be tightly wound about said predetermined pattern of the aforesaid plurality of lightweight metal electrical conductors and extending a predetermined distance therealong for providing retaining engagement thereof and electrical conduction therefrom;
second connector means effectively joined to the other end of said central strain means for attachment of auxiliary devices thereto, so as to be towed thereby;
surface craft means effectively mechanically attached to said first connector means for providing towing attachment therefor;
electrical power generating means attached to said surface craft means for support thereby, and effectively electrically attached to said first connector means for supplying electrical energy thereto;
second electrode means effectively mechanically attached to said surface craft for towing support thereby and effectively connected with said electrical power generating means for providing a return current path via water conduction from said first electrode means;
tow line means effectively mechanically connected at one end thereof to said surface craft means for transmission of towing forces thereto; and
aircraft tractor vehicle means connected to the other end of said tow line means for transmitting towing force therethrough, so as to propel said surface craft means through said body of water.

* * * * *